US012791387B2

(12) United States Patent
Nishida

(10) Patent No.: US 12,791,387 B2
(45) Date of Patent: Nov. 10, 2026

(54) TWO-STAGE COMMON-MODE FEEDBACK CIRCUIT AND FULLY DIFFERENTIAL OPERATIONAL AMPLIFIER INCLUDING THE SAME

(71) Applicant: LITE-ON SINGAPORE PTE. LTD., Singapore (SG)

(72) Inventor: Yoshio Nishida, Singapore (SG)

(73) Assignee: LITE-ON SINGAPORE PTE. LTD., Singapore (SG)

( * ) Notice: Subject to any disclaimer, the term of this patent is extended or adjusted under 35 U.S.C. 154(b) by 422 days.

(21) Appl. No.: 18/527,346

(22) Filed: Dec. 3, 2023

(65) Prior Publication Data

US 2024/0223144 A1 Jul. 4, 2024

(30) Foreign Application Priority Data

Dec. 30, 2022 (SG) ........................... 10202260647U

(51) Int. Cl.
*G01J 3/36* (2006.01)
*G01N 33/483* (2006.01)
(Continued)

(52) U.S. Cl.
CPC ............ *G01J 3/36* (2013.01); *G01N 33/4833* (2013.01); *G01S 17/04* (2020.01); *G02B 1/002* (2013.01);
(Continued)

(58) Field of Classification Search
CPC ..... G01J 3/36; G01J 2003/2806; G01S 17/04; G01N 33/4833; G01N 2021/3568;
(Continued)

(56) References Cited

U.S. PATENT DOCUMENTS 5,281,924 A * 1/1994 Maloberti ........... H03F 3/45192 330/253
8,174,317 B2 * 5/2012 Isoda .................... H03F 3/3022 330/253
(Continued)

FOREIGN PATENT DOCUMENTS

CN 102545805 B 5/2017
CN 109067371 A 12/2018
(Continued)

OTHER PUBLICATIONS

Figueiredo et al., "A Two-Stage Fully Differential Inverter-Based Self-Biased CMOS Amplifier With High Efficiency," IEEE Transactions on Circuits and Systems, vol. 58, No. 7, Jul. 2011 (Year: 2011).*

*Primary Examiner* — Hafizur Rahman
(74) *Attorney, Agent, or Firm* — Li & Cai Intellectual Property Office

(57) ABSTRACT

A two-stage common-mode feedback (CMFB) circuit and a fully differential operational amplifier are provided. The two-stage CMFB circuit includes a first CMFB circuit and a second CMFB circuit. The first CMFB circuit includes a first CMFB component that receives a first differential pair of output signals of the first amplifier and a first reference signal. The first CMFB component generates a first control signal to regulate a first common-mode voltage of the first amplifier to a first reference voltage of the first reference signal. The second CMFB circuit includes a second CMFB component that receives a second differential pair of output signals of the second amplifier and a second reference signal. The second CMFB component generates a second control signal according to a second reference signal, so as
(Continued)

to regulate a second common-mode voltage of the second amplifier to a second reference voltage of the second reference signal.

10 Claims, 4 Drawing Sheets

(51) Int. Cl.

| | |
|---|---|
| ***G01S 17/04*** | (2020.01) |
| ***G02B 1/00*** | (2006.01) |
| ***G02B 5/20*** | (2006.01) |
| ***G02B 5/28*** | (2006.01) |
| ***G02B 26/00*** | (2006.01) |
| ***H03F 1/22*** | (2006.01) |
| ***H03F 3/45*** | (2006.01) |
| ***H03F 3/68*** | (2006.01) |
| *G01J 3/28* | (2006.01) |
| *G01N 21/3563* | (2014.01) |

(52) U.S. Cl.

CPC ............. *G02B 5/201* (2013.01); *G02B 5/286* (2013.01); *G02B 26/001* (2013.01); *H03F 1/223* (2013.01); *H03F 3/45237* (2013.01); *H03F 3/45475* (2013.01); *H03F 3/45748* (2013.01); *H03F 3/68* (2013.01); *G01J 2003/2806* (2013.01); *G01N 2021/3568* (2013.01); *G01N 2201/125* (2013.01); *G02B 2207/101* (2013.01); *H03F 2200/165* (2013.01); *H03F 2200/375* (2013.01); *H03F 2203/45151* (2013.01); *H03F 2203/45212* (2013.01)

(58) Field of Classification Search

CPC .. G01N 2201/125; G02B 1/002; G02B 5/201; G02B 5/286; G02B 26/001; G02B 2207/101; H03F 1/223; H03F 3/45237; H03F 3/45475; H03F 3/45748; H03F 3/68; H03F 2200/165; H03F 2200/375; H03F 2203/45151; H03F 2203/45212

USPC .......................................................... 330/133

See application file for complete search history.

(56) References Cited

U.S. PATENT DOCUMENTS

| | | | | |
|---|---|---|---|---|
| 8,552,801 | B2 * | 10/2013 | Myles ................. | H03F 3/45717 330/258 |
| 2005/0206453 | A1 * | 9/2005 | McCalmont ........ | H03F 3/45659 330/259 |
| 2005/0218985 | A1 * | 10/2005 | Lebedev ............. | H03F 3/45654 330/258 |
| 2008/0143439 | A1 * | 6/2008 | Tanimoto ............ | H03F 3/45183 330/252 |
| 2019/0305739 | A1 | 10/2019 | Joo et al. | |
| 2020/0358414 | A1 * | 11/2020 | Li ......................... | H03F 3/4565 |
| 2022/0294403 | A1 | 9/2022 | Yu et al. | |

FOREIGN PATENT DOCUMENTS

| | | | |
|---|---|---|---|
| CN | 115296624 | A | 11/2022 |
| TW | I325223 | B | 5/2010 |

* cited by examiner

TWO-STAGE COMMON-MODE FEEDBACK CIRCUIT AND FULLY DIFFERENTIAL OPERATIONAL AMPLIFIER INCLUDING THE SAME

CROSS-REFERENCE TO RELATED PATENT APPLICATION

This application claims the benefit of priority to Singapore Provisional Patent Application Ser. No. 10202260647U, filed on Dec. 30, 2022, which application is incorporated herein by reference in its entirety.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a circuit and a device, and more particularly to a two-stage common-mode feedback circuit and a fully differential operational amplifier including the same.

BACKGROUND OF THE DISCLOSURE

In the related art, the common-mode feedback circuit (CMFB) is vital to fully differential operational amplifier (op-amp) since the output common-mode level shifts to unwanted high/low end without CMFB.

The conventional CMFBs can force a level of an output common-mode voltage of each stage amplifier to a fixed level that is independent of an operational voltage (power supply voltage) used in the operational amplifier. However, when the operation voltage changes, an amplifier current may vary by a significant amount, which requires a large design margin to secure performance of the operational amplifier (e.g., gain, bandwidth, etc.) within a specification complying with the operation voltage, which results in a more complex design.

SUMMARY OF THE DISCLOSURE

In response to the above-referenced technical inadequacies, the present disclosure provides a two-stage common-mode feedback circuit and a fully differential operational amplifier including the same.

In order to solve the above-mentioned problems, one of the technical aspects adopted by the present disclosure is to provide a fully differential operational amplifier, which includes a first stage and a second stage. The first stage includes a first amplifier and a first common-mode feedback (CMFB) circuit. The first amplifier is configured to amplify a difference signal between a first differential pair of input signals and to output a first differential pair of output signals. The first CMFB circuit includes a first CMFB component that receives the first differential pair of output signals and a first reference signal. The first CMFB component is configured to generate a first control signal for the first amplifier according to the first differential pair of output signals and the first reference signal, so as to regulate a first common-mode voltage of the first amplifier to a first reference voltage of the first reference signal. The second stage is connected to the first stage and includes a second amplifier and a second CMFB circuit. The second amplifier is configured to amplify another difference signal between the first differential pair of output signals and to output a second differential pair of output signals. The second CMFB circuit includes a second CMFB component that receives the second differential pair of output signals and a second reference signal. The second CMFB component is configured to generate a second control signal according to the second differential pair of output signals and the second reference signal, so as to regulate a second common-mode voltage of the second amplifier to a second reference voltage of the second reference signal.

Therefore, in the two-stage common-mode feedback circuit and the fully differential operational amplifier including the same provided by the present disclosure, by employing the first CMFB component that uses an operation voltage (power supply voltage)-dependent reference signal, the current variation over the specification of the power supply voltage can be reduced, thereby facilitating the circuit design for the operational amplifier with two stages.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
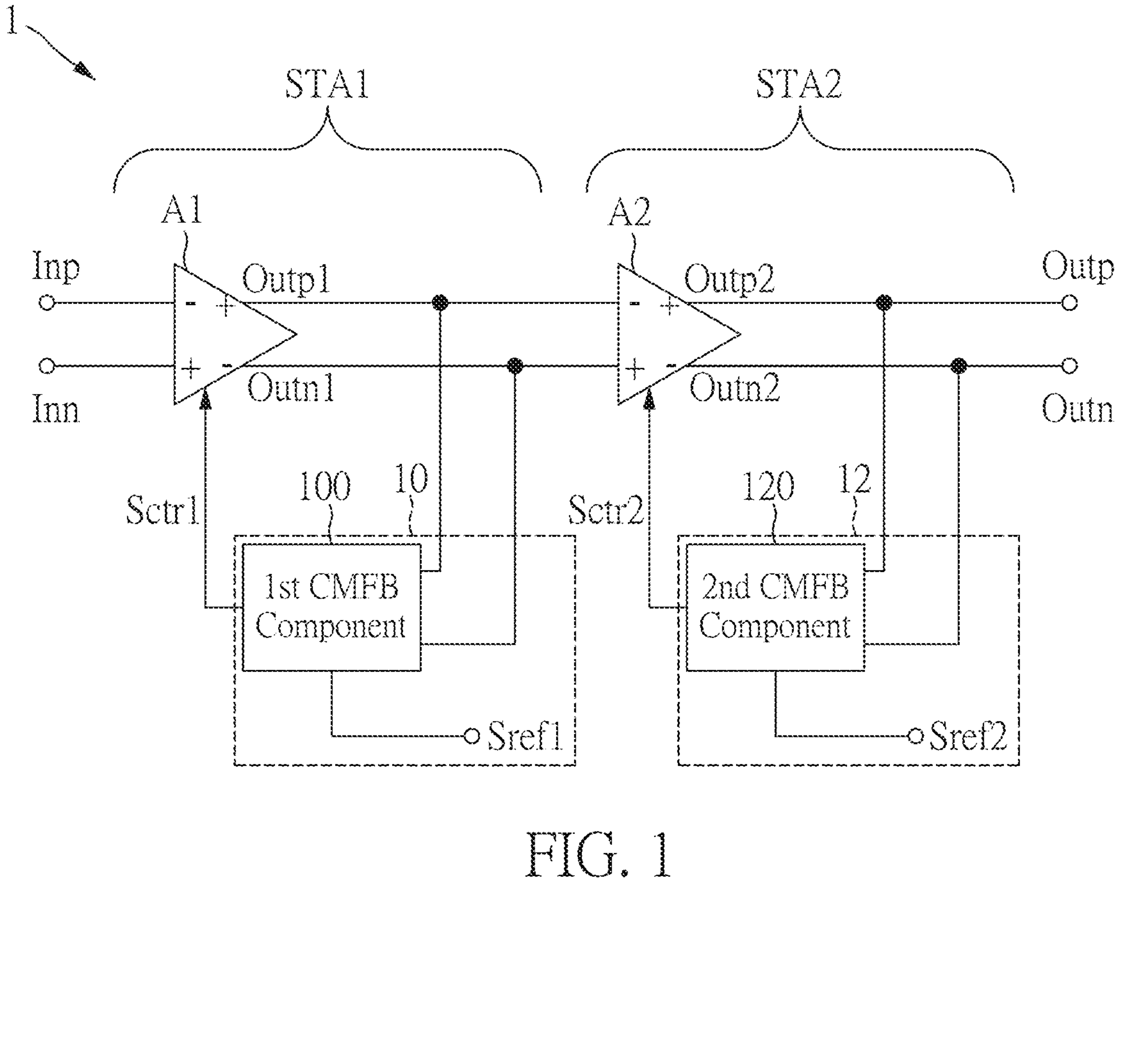
FIG. 1 is a schematic diagram showing a fully differential operational amplifier according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as “first,” “second” or “third” can be used to describe various components, signals or the like, which are for distinguishing one component/signal from another one only, and are not intended to, nor should be construed to impose any substantive limitations on the components, signals or the like.

FIG. 1 is a schematic diagram showing a fully differential operational amplifier according to one embodiment of the present disclosure. Referring to FIG. 1, one embodiment of the present disclosure provides a fully differential operational amplifier 1, which includes a first stage STA1 and a second stage STA2 connected in series.

The first stage STA1 includes a first amplifier A1 and a first common-mode feedback (CMFB) circuit 10. The first amplifier A1 can be a differential operational amplifier, and can be configured to amplify a difference signal between a first differential of input signals Inp and Inn, and output a first differential pair of output signals Outp1 and Outp2.

The first CMFB circuit 10 can include a first CMFB component 100 that receives the first differential pair of output signals Outp1 and Outn1 and a first reference signal Sref1. The CMFB component 100 can be a circuit that at least includes a common-mode voltage detector and a comparator, the common-mode voltage detector is used to sense a common-mode voltage of the first amplifier A1, compare the sensed common-mode voltage with a designated reference voltage, and feed back the control signal Sctr11 to the first (fully-differential) amplifier A1 with a purpose of assimilating the common-mode voltage to desired voltage level. Various types of CMFB circuits known to those skilled in the art, such as a simple operational amplifier, a common-mode sense current amplifier with a transconductance level sense circuit, and the like, can be utilized in the present disclosure.

Therefore, the first CMFB component 100 can be configured to generate a first control signal Sctr1 for the first amplifier A1 according to the first differential pair of output signals Outp1 and Outn1 and the first reference signal Sref1, so as to regulate a first common-mode voltage of the first amplifier A1 to a first reference voltage of the first reference signal Sref1.

The second stage STA2 is connected to the first stage STA1 and includes a second amplifier A2 and a second CMFB circuit 12. The second amplifier A2 can be a fully differential amplifier that is configured to amplify another difference signal between the first differential pair of output signals Outp1 and Outn1, and output a second differential pair of output signals Outp2 and Outn2 through output terminals Outp and Outn, respectively.

Similar to the first CMFB circuit 10, the second CMFB circuit 12 includes a second CMFB component 120 that receives the second differential pair of output signals Outp2 and Outn2 and a second reference signal Sref2. The second CMFB component 120 is configured to generate a second control signal according to the second differential pair of output signals Outp2 and Outn2 and the second reference signal Sref2, so as to regulate a second common-mode voltage of the second amplifier A2 to a second reference voltage of the second reference signal Sref2.

Specifically, in order to facilitate the circuit design for the fully differential operational amplifier 1, a current variation over an operation voltage (e.g., a power supply voltage) supplied by a common power source that is used by the first amplifier A1 and the second amplifier A2 should be reduced. A level of the second reference signal Sref2 is usually designed to half of the operation voltage, while the first reference signal Sref1 need to be designed carefully for above objective. In this case, the first reference voltage can be obtained by subtracting a predetermined voltage from the operation voltage (e.g., Vdd−x), and the second reference voltage can be a constant value that equals to the operation voltage multiplied with a set value (e.g., y*Vdd) of ½, for example, and details of which will be illustrated hereinafter.

Figure 2:
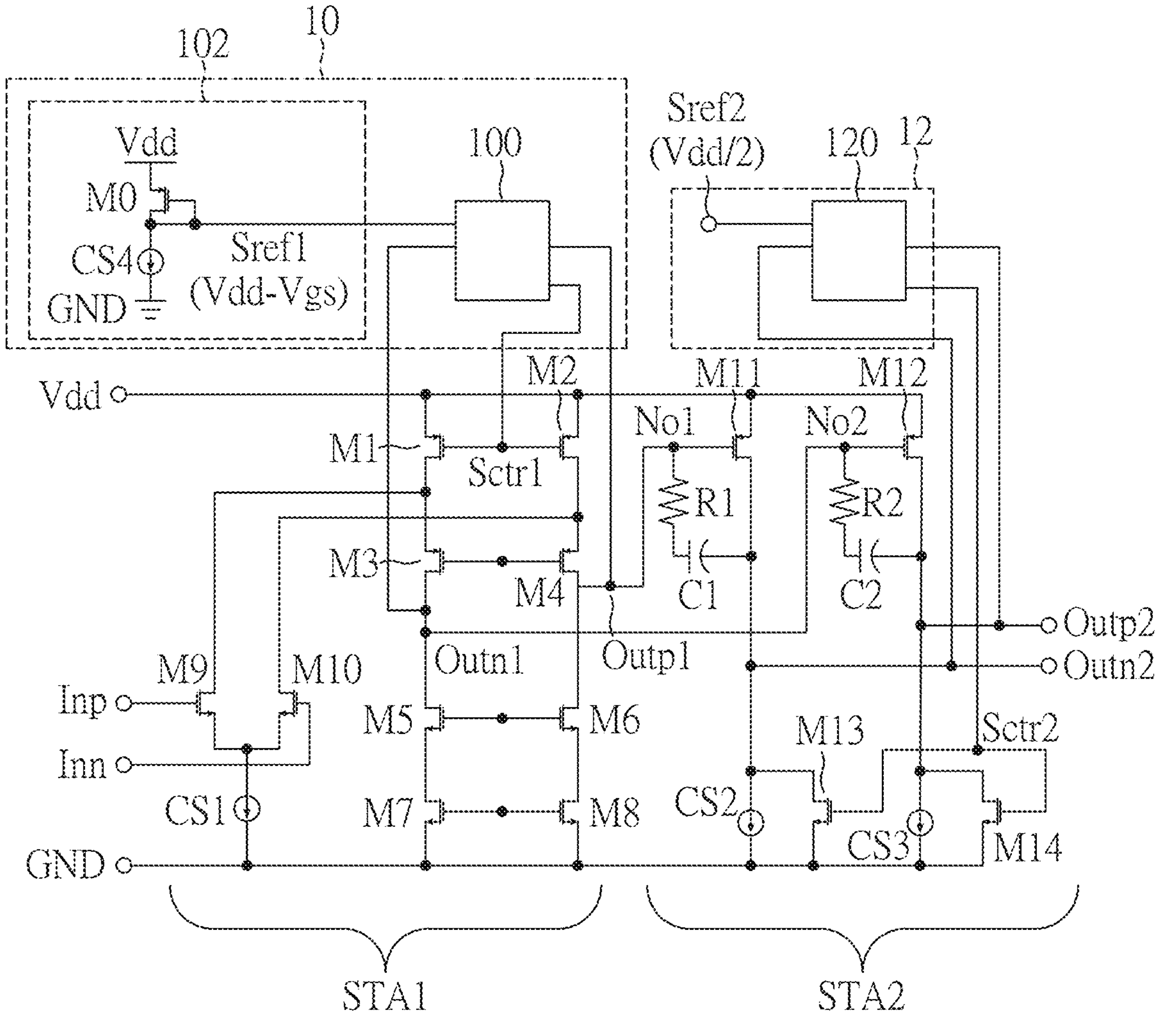
FIG. 2 is a circuit layout of the fully differential operational amplifier according to one embodiment of the present disclosure.

Further reference is made to FIG. 2, which is a schematic circuit diagram of the fully differential operational amplifier according to one embodiment of the present disclosure.

Those of ordinary skill in the art can recognize a resistor symbol, a capacitor symbol, and a MOSFET (metal-oxide semiconductor field effect transistor) symbol, for both PMOSFET and NMOSFET, and can identify a “source” terminal, a “gate” terminal, and a “drain” terminal of a MOSFET. Those of ordinary skills in the art can read schematics of a circuit comprising resistors, capacitors, NMOSFET, and PMOSFET, and do not need a verbose description about how one transistor, resistor, or capacitor connects with another in the schematics.

As shown in FIG. 2, an exemplary example of fully differential operational amplifier 1 is provided, in which the first amplifier A1 includes MOSFETs M1 through M10 and a constant current source CS1, and the second amplifier A2 includes MOSFETs M11 through M14, a first resistor R1, a first capacitor C1, a second resistor R2, a second capacitor C2, and constant current sources CS2 and CS3. Furthermore, the first amplifier A1 and the second amplifier A2 are connected to a common power source that provides the operation voltage Vdd. More specifically, sources of the MOSFETs M1 and M2 of the first amplifier A1 and sources of the MOSFETs M11 and M12 are connected to the common power source that provides the operation voltage Vdd.

However, the aforementioned details are disclosed for exemplary purposes only, and are not meant to limit the scope of the present disclosure.

It should be noted that, in the conventional differential amplifier with CMFB circuits, the first differential pair of output signals Outp1 and Outn1 and the second differential pair of output signals Outp2 and Outn2 are generally regulated to a predetermined common-mode voltage, which is Vdd/2. Therefore, the first differential pair of output signals Outp1 and Outn1 that is regulated to Vdd/2 is output to the second stage STA2, so as to generate voltages of Vdd/2 at a first output node No1 between a drain of the MOSFET M4 and a gate of the MOSFET M11 and a second output node No2 between a drain of the MOSFET M3 and a gate of the MOSFET M12. Under such a premise, amplifier currents of the second amplifier A2 significantly vary as the operation voltage (Vdd) since a source-gate voltage of the MOSFET M11 and a source-gate voltage of the MOSFET M12 are kept at Vdd/2, which is dependent of the operation voltage Vdd.

To address the above variation issue, the first CMFB circuit 10 further includes a reference signal source 102 that is used to provide the first reference signal Sref1 with the designed first reference voltage.

In the present embodiment, the reference signal source 102 can include a MOSFET M0 and a constant current source CS4. The MOSFET M0 has a first end (e.g., source) connected to the operation voltage Vdd, a second end (e.g., drain), and a third end (e.g., gate) connected to the second end and a reference terminal of the first CMFB component 100. The constant current source CS4 is connected between the second end and a ground end. Therefore, the designed first reference voltage can be obtained by subtracting a voltage between the first end and the third end of the MOSFET M0, which is a gate-to-source voltage Vgs, and the first reference voltage is Vdd−Vgs. In the present embodiment, the voltage Vgs is taken as the predetermined voltage that is independent of the operation voltage Vdd.

Therefore, the first CMFB component 100 can generate the first control signal Sctr1 at a node between gates of the MOSFETs M1 and M2 of the first amplifier A1 according to the first differential pair of output signals Outp1 and Outn1 and the first reference signal Sref1, so as to regulate the first common-mode voltage of the first amplifier A1 to the first reference voltage (i.e., Vdd−Vgs) of the first reference signal Sref1.

In this regard, the first differential pair of output signals Outp1 and Outn1 that is regulated to Vdd−Vgs is output to the second stage STA2, so as to generate voltages of Vgs between an operation voltage node NVdd (that receives the operation voltage Vdd) and the first output node No1 and between the operation voltage node NVdd and the second output node No2, respectively.

Under such a premise, variations of the amplifier currents of the second amplifier A2 over the operation voltage Vdd can be reduced since the source-to-gate voltages of the MOSFETs M1 and M12 are kept at Vgs, which is independent of the operation voltage Vdd of the common power source.

Figure 3:
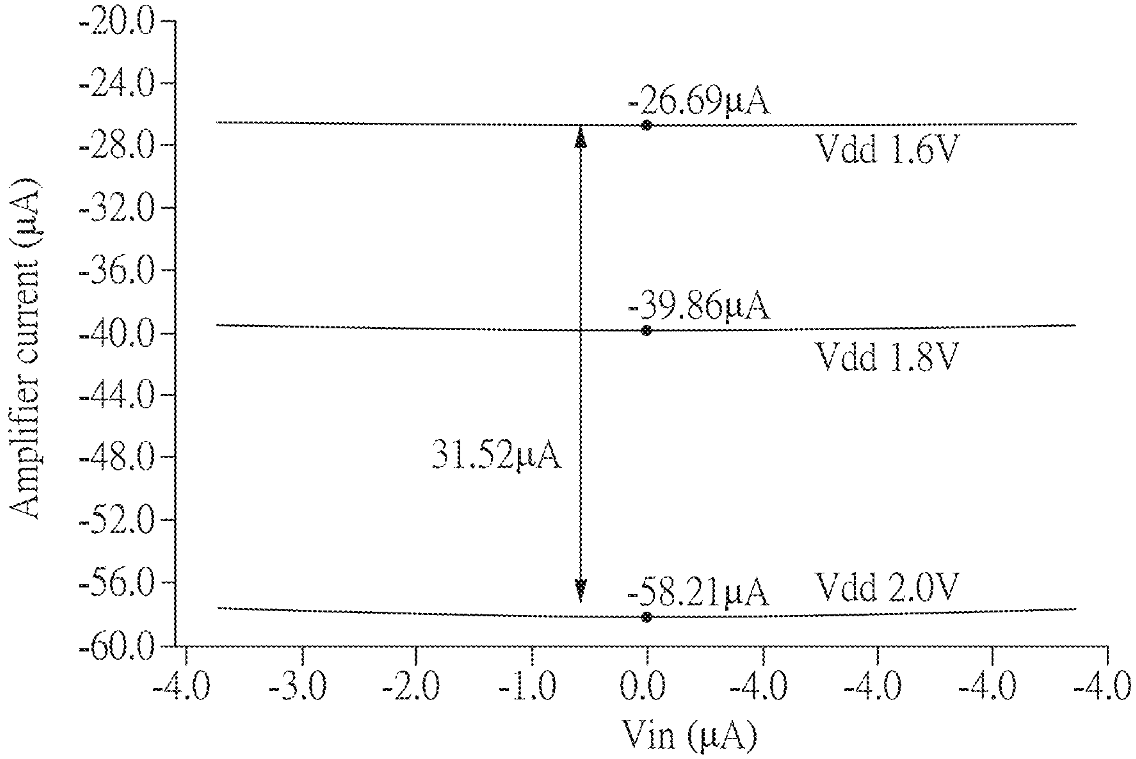
FIG. 3 is a waveform diagram showing amplifier currents versus input voltage Vin over different power supply voltages with conventional CMFB circuits.
Figure 4:
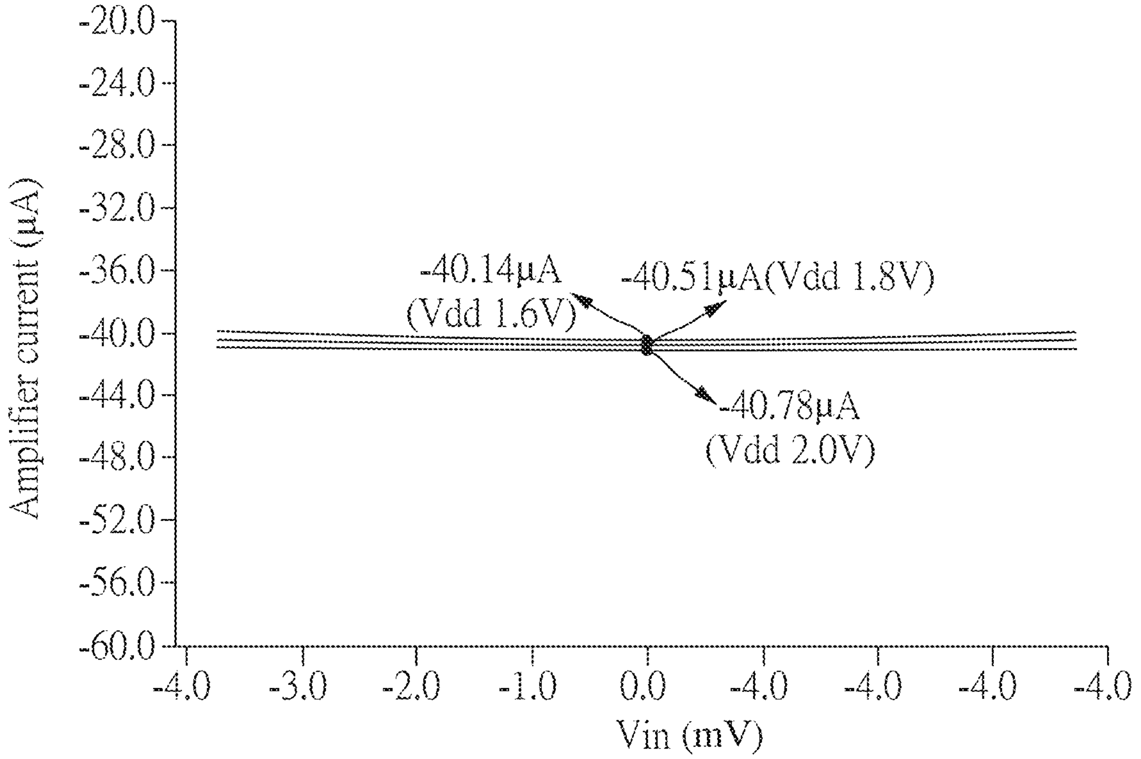
FIG. 4 is a waveform diagram showing amplifier currents versus input voltage Vin over different power supply voltages of the fully differential operational amplifier with two-stage CMFB circuit according to one embodiment of the present disclosure.

FIG. 3 is a waveform diagram showing amplifier currents versus input voltage Vin over different power supply voltages with conventional CMFB circuits, and FIG. 4 is a waveform diagram showing amplifier currents versus input voltage Vin over different power supply voltages of the fully differential operational amplifier with two-stage CMFB circuit according to one embodiment of the present disclosure.

As can be seen from FIGS. 3 and 4, the amplifier currents with the conventional CMFB circuits significantly vary as the power supply voltage (i.e., the operation voltage Vdd) since voltage levels of the first output node No1 and the second output node No2 is dependent of the operation voltage Vdd. In FIG. 3, a variation between the amplifier currents under Vdd of 1.6V and 2.0V reaches about 31.52 μA.

In contrast, comparing FIG. 4 with FIG. 3, the variation of the amplifier currents with the two-stage CMFB circuit provided by the present disclosure over the operation voltage Vdd can be significantly reduced since voltage levels between the operation voltage node NVdd and the first output node No1 and between the operation voltage node NVdd and the second output node No2 are kept at Vgs, which is independent of the operation voltage Vdd of the common power source. In FIG. 4, a variation between the amplifier currents under Vdd of 1.6V and 2.0V can be reduced to about 0.64 μA.

Beneficial Effects of the Embodiments

In conclusion, in the two-stage common-mode feedback circuit and the fully differential operational amplifier including the same provided by the present disclosure, by employing the CMFB component that uses an operation voltage (Vdd)-dependent reference signal, the current variation over the operation voltage specification can be reduced, thereby facilitating the circuit design for the operational amplifier with two stages.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A fully differential operational amplifier, comprising:

a first stage, including:

a first amplifier configured to amplify a difference signal between a first differential pair of input signals and output a first differential pair of output signals; and a first common-mode feedback (CMFB) circuit including a first CMFB component that receives the first differential pair of output signals and a first reference signal, wherein the first CMFB component is configured to generate a first control signal for the first amplifier according to the first differential pair of output signals and the first reference signal, so as to regulate a first common-mode voltage of the first amplifier to a first reference voltage of the first reference signal; and a second stage connected to the first stage, wherein the second stage includes:

a second amplifier configured to amplify another difference signal between the first differential pair of output signals and output a second differential pair of output signals; and a second CMFB circuit including a second CMFB component that receives the second differential pair of output signals and a second reference signal, wherein the second CMFB component is configured to generate a second control signal according to the second differential pair of output signals and the second reference signal, so as to regulate a second common-mode voltage of the second amplifier to a second reference voltage of the second reference signal.

2. The fully differential operational amplifier according to claim 1, wherein the first reference voltage is obtained by subtracting a predetermined voltage from an operation voltage.

3. The fully differential operational amplifier according to claim 2, wherein the set value is ½, and the predetermined voltage is independent from the operation voltage.

4. The fully differential operational amplifier according to claim 3, wherein the first CMFB circuit further includes:

a reference signal source, including:

a first transistor having a first end connected to the operation voltage, a second end, and a third end connected to the second end and the first CMFB component; and a first constant current source connected between the second end and a ground end.

5. The fully differential operational amplifier according to claim 3, wherein the first amplifier and the second amplifier are connected to a common power source that provides the operation voltage.

6. A two-stage common-mode feedback (CMFB) circuit, adapted for a fully differential operational amplifier that includes a first amplifier and a second amplifier connected in series, and the two-stage CMFB circuit comprising:

a first CMFB circuit including a first CMFB component that receives a first differential pair of output signals of the first amplifier and a first reference signal, wherein the first CMFB component is configured to generate a first control signal for the first amplifier according to the first differential pair of output signals and the first reference signal, so as to regulate a first common-mode voltage of the first amplifier to a first reference voltage of the first reference signal; and a second CMFB circuit including a second CMFB component that receives a second differential pair of output signals of the second amplifier and a second reference signal, wherein the second CMFB component is configured to generate a second control signal according to the first differential pair of output signals and the reference signal, so as to regulate a second common-mode voltage of the second amplifier to a second reference voltage of the second reference signal.

7. The two-stage CMFB circuit according to claim 6, wherein the first reference voltage is obtained by subtracting a predetermined voltage from an operation voltage.

8. The two-stage CMFB circuit according to claim 7, wherein the predetermined voltage is independent from the operation voltage.

9. The two-stage CMFB circuit according to claim 8, wherein the first CMFB circuit further includes:

a reference signal source, including:

a first transistor having a first end connected to the operation voltage, a second end, and a third end connected to the second end and the first CMFB component; and a first constant current source connected between the second end and a ground end.

10. The two-stage CMFB circuit according to claim 9, wherein the first amplifier and the second amplifier are connected to a common power source that provides the operation voltage.

* * * * *